United States Patent
Kroll

(10) Patent No.: US 7,254,440 B1
(45) Date of Patent: Aug. 7, 2007

(54) IMPLANTABLE ISCHEMIA AND MYOCARDIAL INFARCTION MONITOR AND METHOD

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 616 days.

(21) Appl. No.: 10/765,508

(22) Filed: Jan. 26, 2004

(51) Int. Cl.
*A61B 5/0452* (2006.01)
*A61B 5/0468* (2006.01)

(52) U.S. Cl. .................. 600/517; 600/516; 607/25

(58) Field of Classification Search ............ None
See application file for complete search history.

(56) References Cited

U.S. PATENT DOCUMENTS

| | | | |
|---|---|---|---|
| 5,779,645 A * | 7/1998 | Olson et al. ............ 600/518 |
| 6,112,116 A | 8/2000 | Fischell et al. ............ 600/517 |
| 6,272,379 B1 | 8/2001 | Fischell et al. ............ 607/5 |
| 7,181,269 B1 * | 2/2007 | Kroll ............ 600/517 |
| 2002/0091330 A1 * | 7/2002 | MacAdam et al. ............ 600/509 |
| 2003/0023175 A1 | 1/2003 | Arzbaecher et al. ............ 600/509 |
| 2003/0055461 A1 | 3/2003 | Girouard et al. ............ 607/17 |
| 2004/0093034 A1 * | 5/2004 | Girouard et al. ............ 607/3 |
| 2005/0010122 A1 * | 1/2005 | Nearing et al. ............ 600/509 |

* cited by examiner

*Primary Examiner*—Kristen Droesch Mullen

(57) ABSTRACT

An implantable ischemia detecting devices generates a plurality of electrograms for analysis. A processor integrates the ST segment and T wave of each electrogram and normalizes the resulting integral by a normalizing factor to provide a ST segment score and T wave score, respectively. The ST segment and T wave scores are then utilized to compute a total ST segment and T wave score for analysis in detecting or monitoring ischemia of a patient's heart.

17 Claims, 4 Drawing Sheets

IMPLANTABLE ISCHEMIA AND MYOCARDIAL INFARCTION MONITOR AND METHOD

FIELD OF THE INVENTION

The present invention generally relates to an apparatus and method for assisting in the diagnosis of ischemia of a human heart. The present invention is more particularly directed to an apparatus fully implantable beneath the skin of a patient for determining the presence or absence of ischemia or a myocardial infarct of the human heart.

BACKGROUND

Patients who suffer what is commonly called a heart attack most often experience an episode of ischemia or myocardial infarction. Myocardial infarction is a necrosis of cardiac tissue brought on by a reduction in blood flow to the infarcted area caused by either a chronic obstruction in an artery or an acute obstruction such as a thrombus in the artery.

To monitor patients for myocardial infarction, physicians may rely upon periodic EKGs (electrocardiograms) which generally require as many as ten leads to be attached to the patient. In addition, after the EKG, physicians then generally require the patient to take a stress test wherein the patient is caused to run on a treadmill until the patient is essentially exhausted to stress the heart. During and after the treadmill exercise the twelve lead EKG is used to determine if the heart continues to receive adequate blood supply while under the stress conditions. Obviously such monitoring is inconvenient to the patient. Physicians may also rely upon Holtor monitoring recordings which may last from 24 to 48 hours. These additional monitoring techniques are equally as inconvenient and in addition, are also annoying. Since all of these monitoring techniques can, at best, only be administered periodically as a practical matter, and because restenosis and thus future episodes of myocardial infarction are unpredictable events, all too often, a myocardial infarction or restenosis problem may not be detected until the patient experiences pain or suffers an episode of myocardial infarction. Unfortunately, research has shown that pain is not a reliable indicator of ischemia.

Patients who have a myocardial infarction are generally treated with drugs and angioplasty to open the artery. Each of the above-mentioned therapeutic techniques is effective in reestablishing blood flow through the effected artery. However, for each therapy, there is a percentage of patients that experience restenosis (reclosure of the artery) after therapy. Restenosis is largely an unpredictable event and the time required for the reclosure to occur may range from a matter of hours to years.

From the foregoing, it can be seen that for some patients, it is very desirable to monitor for ischemia or the presence of a myocardial infarction. Many of these patients will already have an implanted cardiac stimulation device such as a pacemaker or a combined pacemaker and defibrillator.

Implantable cardiac devices have been proposed in the art for detecting for and monitoring ischemia. Many of these devices may be solely for monitoring or incorporated into pacemakers and defibrillators. With modern day storage technology and telemetry, these devices are capable of collecting and communicating large amounts of ischemia data. Dealing with this prolific data in a meaningful way remains a challenge. The present invention addresses these issues.

SUMMARY

What is described herein is an implantable ischemia detecting device comprising at least two electrodes that sense cardiac activity of a heart and a sensing circuit coupled to the at least two electrodes that provides an electrogram of the sensed cardiac activity. The device further comprises a processor comprising an integrator that provides an integral of a selected feature of the electrogram and a normalizer that normalizes the integral by a normalizing factor to provide an electrogram feature score and an analyzer that provides an ischemia indication when the electrogram feature score satisfies a given criteria.

The selected electrogram feature may be at least one of an ST segment and a T wave. The normalizing factor may be one of an R wave amplitude and an R wave amplitude difference. The normalizer may be a divider and the divider may further divide the integral by the time duration of the selected feature.

The sensing circuit and processor may be enclosed within a conductive case and the at least two electrodes may include the case. The at least two electrodes may further include one of a ring electrode and a tip electrode. The at least two electrodes may be a ring electrode and a tip electrode.

The at least two electrodes may provide a plurality of cardiac activity sensing electrode configurations resulting in a plurality of electrograms and electrogram feature scores. The processor may further comprises a combiner that provides a combined electrogram feature score, and the analyzer may then analyze the combined electrogram feature score.

The combiner may be a summer that adds the electrogram feature scores to provide the combined electrogram feature score. Alternatively, the combiner may select a maximum one of the electrogram feature scores as the combined electrogram feature score.

The normalizer may normalize the combined electrogram feature score by a second normalizing factor. The second normalizing factor may be heart rate.

The analyzer may apply a threshold metric to the combined electrogram feature score. A combined electrogram feature score may be provided by the device for each one of a plurality of cardiac cycles. The device may further comprise a reporter that reports a percentage of the combined feature scores which exceed the threshold metric. The analyzer may provide a continuous metric of the combined electrogram feature scores. The device may further comprise a classifier that classifies the combined electrogram feature scores by one of heart rate, posture and activity level.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Figure 1:
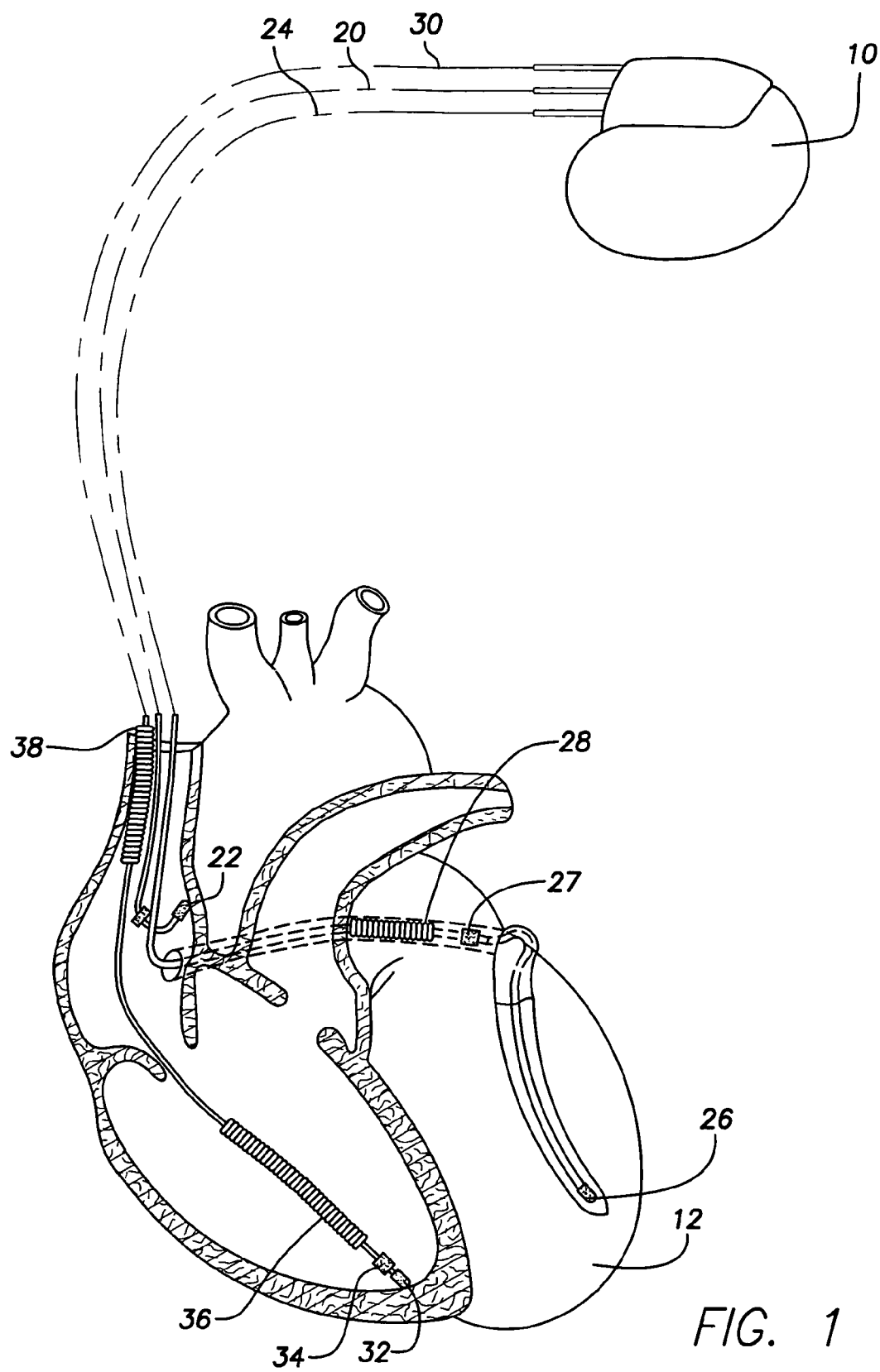
FIG. 1 is a simplified diagram illustrating an implantable stimulation device which may include an ischemia monitor.

As shown in FIG. 1, there is a stimulation device 10 in electrical communication with a patient's heart 12 by way of three leads, 20, 24 and 30, suitable for delivering multi-chamber stimulation and shock therapy and which includes an ischemia monitor according to one embodiment of the present invention. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
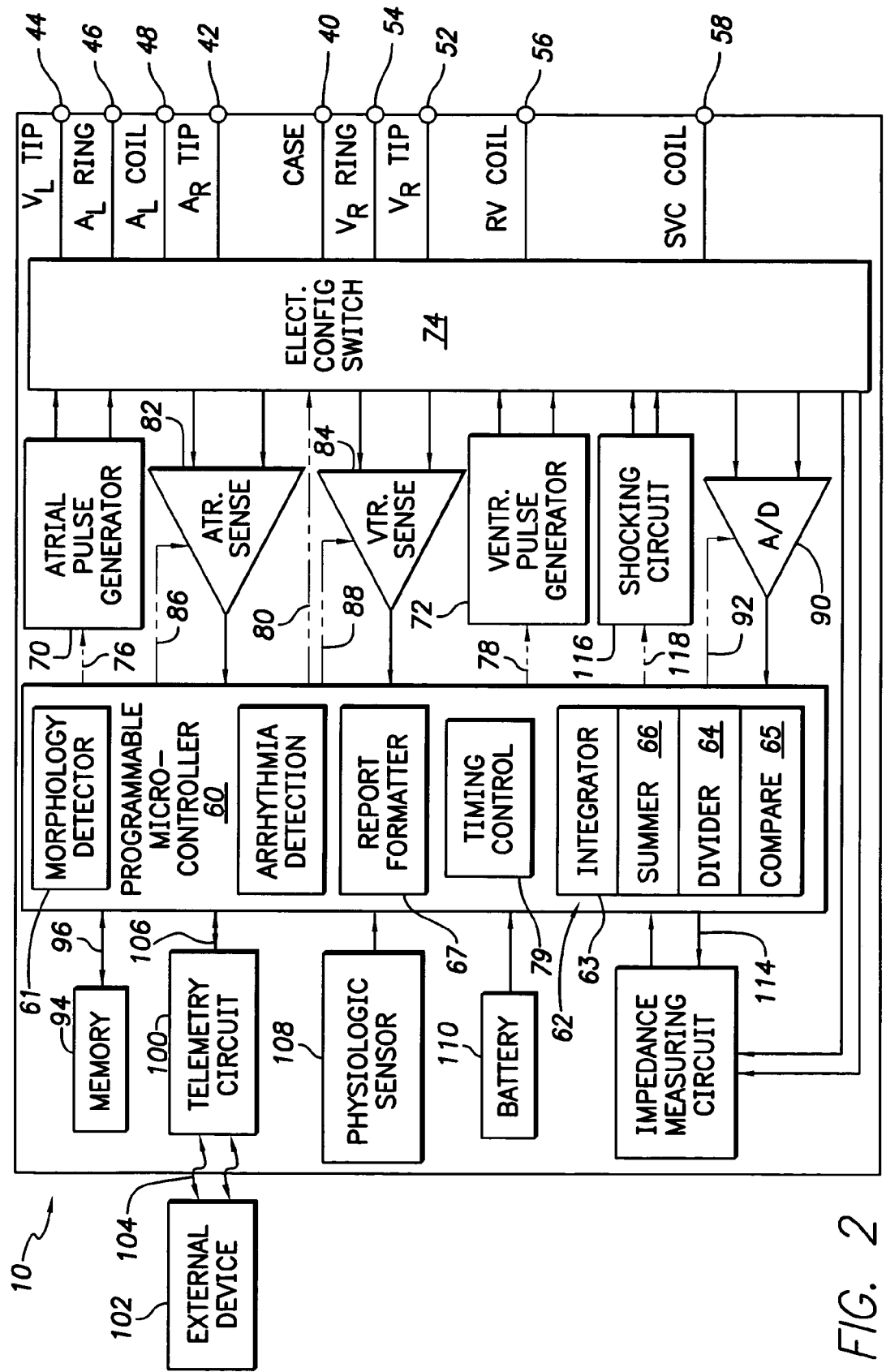
FIG. 2 is a functional block diagram of the implantable stimulation device of FIG. 1 illustrating the basic elements of the stimulation device along with an ischemia monitor according to one embodiment.

As illustrated in FIG. 2, a simplified block diagram is shown of the implantable stimulation device 10. While a particular multi-chamber device is shown, this is for illustration purposes only, and one of skill in the art could readily duplicate, eliminate or disable the appropriate circuitry in any desired combination to provide a device having an ischemia monitor according to the present invention and which is capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for "unipolar" pacing and sensing electrode configurations. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy and which performs electrogram processing and analysis for ischemia monitoring according to an embodiment of the present invention. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

In accordance with this embodiment of the present invention, cardiac signals are also applied to the inputs of a data acquisition system 90. More specifically, a plurality of electrograms are conveyed to the data acquisition system 90 which digitizes the electrograms before they are stored in a memory 94 for further processing in accordance with this embodiment. The cardiac signals result from cardiac activity sensing with a plurality of sensing electrode configurations. These electrode configurations may include ventricular tip electrode 32 and ventricular ring electrode 34, ventricular tip electrode 32 and the case 40, ventricular ring electrode 34 and the case 40, and/or any one of the other tip electrodes and the case 40. Each electrode configuration may have its own dedicated acquisition system or the plurality of electrograms may be multiplexed prior to digitization. These electrograms result by selecting the electrode configurations with switch 74 for sensing between the various electrode combinations. As will be appreciated by those skilled in the art, alternative sensing electrode configurations may be selected with switch 74 without departing from the present invention.

Programmable operating parameters used by the microcontroller 60 are also stored in memory 94 and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The physiologic sensor 108 may further include a posture sensor. The posture sensor may detect the posture of the patient between a fully upright position and a supine position. To that end, the posture sensor may include accelerometers which detect acceleration in three mutually transverse directions. The signals from the posture sensor may be provided to a control circuit to generate different control signals. A first control signal may be a logical "1" if the patient is in an upright position and a logical "0" if the patient is in a supine position. A second control signal may be a multiple-bit binary fractional factor between 0 and 1 representing the posture of the patient. For example, the fractional factor may vary from 0, representing the patient in a supine position, to 1, representing the patient in a fully upright position. One such posture sensor is fully described in copending U.S. Pat. No. 6,466,821, issued Oct. 15, 2002, which patent is owned by the assignee of the present invention and incorporated herein in its entirety by reference.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, in accordance with the present invention, the device 10 further includes an ischemia detector 62. The ischemia detector 62, according to this embodiment of the present invention processes each of the stored electrograms and analyzes the processing results to detect or monitor ischemia and to provide a suggested diagnosis.

Prior to the electrogram processing by the ischemia detector 62, electrogram features, and more particularly, the ST segments and T waves are isolated in each of the electrograms. This is accomplished, for example, with morphology detector 61. Such ST segment and T wave isolation is well known in the art.

Figure 3:
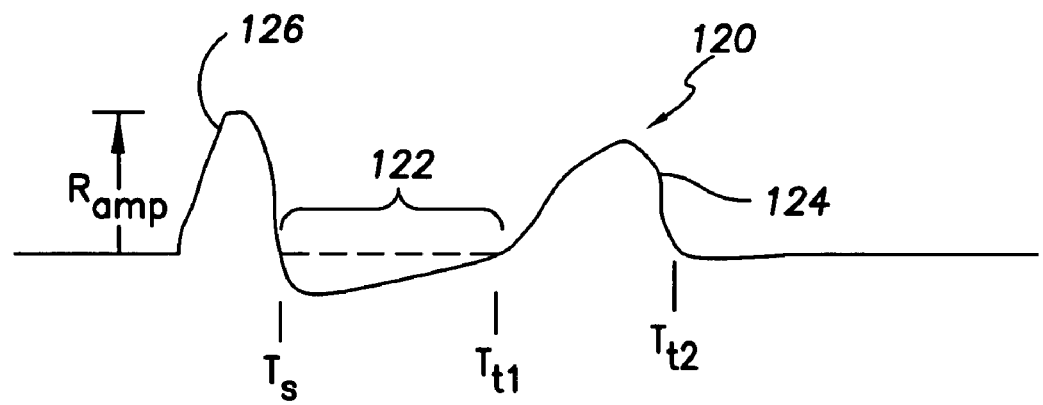
FIG. 3 shows an illustrative electrogram having an ST segment depression indicative of ischemia.
Figure 4:
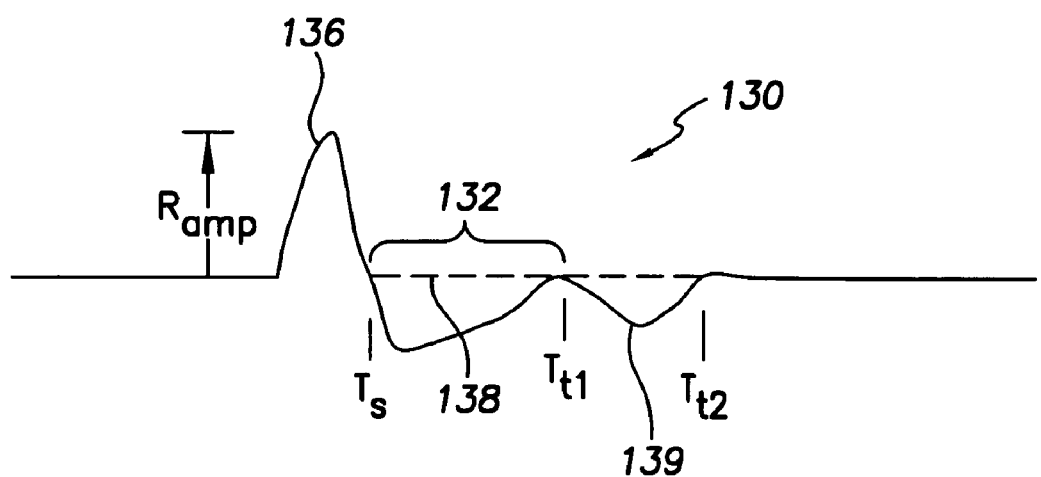
FIG. 4 shows an illustrative electrogram having both an ST segment depression and a T wave inversion indicative of ischemia.

The isolated ST segments and T waves are then processed and analyzed. First an integrator 63 integrates each ST segment and T wave over its duration to provide an ST segment integral and a T wave integral for each electrogram. FIGS. 3 and 4 show illustrative electrograms indicative of ischemia.

In FIG. 3, electrogram 120 includes an isolated ST segment 122 and an isolated T wave 124. Also illustrated is the amplitude ($R_{amp}$) of the R wave 126. In FIG. 4, electrogram 130 includes an isolated ST segment 132 and an isolated T wave 134. Also illustrated is the amplitude ($R_{amp}$) of the R wave 136.

As may be noted in FIG. 3, the ST segment 122 is depressed from a baseline 128. This is indicative of ischemia. In FIG. 4, both the ST segment 132 and T wave 134 are depressed from baseline 138. Such a T wave depression is also indicative of ischemia.

In performing the integration, the integrator 63 integrates the ST segment 122 from $T_s$ to $T_{t1}$ and the T wave 124 from $T_{t1}$ to $T_{t2}$. Similarly, the integrator 63 integrates the ST segment 132 from $T_s$ to $T_{t1}$. Preferably, the absolute values of the ST segments and T waves are integrated. Still further, for enhanced accuracy, the T wave integral may be the integral of the absolute value of the difference between the T waves and a normal, non-ischemic T wave defined by the function X(t).

Each of the integrals will be in units of volt seconds. To render each integral dimensionless, the integrals are normalized. Each of the integrals may be normalized by a divider 64. First the integrals are divided by the duration of the respective isolated feature. Hence, the ST segment integrals may be divided by $T_{t1}-T_s$ and the T wave segment integrals may be divided by $T_{t2}-T_{t1}$. Also, each integral may be divided by the R wave amplitude ($R_{amp}$). This is especially relevant for the ST segment interval because external stress test research suggests that normalizing the ST segment change by the R wave amplitude improves accuracy for diagnosing ischemic heart disease. After normalizing, the final results provide, for each sensing vector, an ST segment score and a T wave score. Summarizing the foregoing, the scores may be expressed as follows:

$$STscore = \frac{1}{R_{amp}} \int_{T_s}^{T_{t1}} v(t)dt \left[\frac{1}{T_{t1}-T_s}\right] \text{ and}$$

$$T \text{ wave score} = \frac{1}{R_{amp}} \int |x(t)-v(t)|dt \left[\frac{1}{T_{t2}-T_{t1}}\right]$$

Each of the ST segment and T wave scores may be compared to a predetermined standard by the compare circuit 65. If greater than the standard, possible ischemia is present. This decision and the separate ST segment and T wave scores may be stored in memory 94 for later transmission to an external receiver by telemetry circuit 100 after being formatted by the report formatter. It may also be used to trigger delivery of a suitable therapy.

Since multiple ST segments and T wave scores are provided (one for each sense vector) a combined or total score may be developed. For example, the summer 66 may be employed to provide a total score equal to the sum of all of the scores as below:

$$\text{Total } ST \text{ score} = \sum_{\text{vectors } j} ST \text{ score } j;$$

$$\text{Total } T \text{ wave score} = \sum_{\text{vectors } j} T \text{ score } j$$

In an alternate embodiment, the absolute values of the ST segment and T wave scores may be summed. Further, the total score may be the maximum of all of the individual scores so that the impact of ischemia detection with a given electrode configuration is not diminished by the lack of global ischemia. Still further, the total scores may be normalized to heart rate. This would result in a normalized total score which has been multiplied times 60 beats per minute and divided by the heart rate HR (60/HR).

Once a total ST segment and/or T wave score is determined, the result may be applied by compare 65 to a threshold matrix. In one embodiment, the threshold function is a 0 when the normalized total ST segment score is within Z of 0, and 1 if it is greater than Z of O (Z may be 0.2, for example). Thus, a result of 1 would indicate ischemia or a myocardial infarct (MI). In accordance with another embodiment, the threshold metric is made ternary. Hence, the result is 0 when the absolute value of the total normalized score is less than Y, becomes M if the total normalized score is greater than Y, and I if it is less than −Y (Y may be 0.08 to 1, for example). The ternary metric may be especially useful since MI is more often correlated with a positive ST change and exercise induced ischemia is more commonly correlated with negative ST change.

The compare results may be accumulated over time. Periodically, the report formatter 67 formats a burden report for transmission by telemetry circuit 100. The burden report may be, for example, the percentage of each metric result. Hence the report may be the percentage O, M, and/or I results.

According to another embodiment, a more sophisticated version would be to provide a continuous metric. This may be the integral over all time of a weighted sum of the absolute values of the normalized total ST segment scores and T wave scores. This combines the ST segment and the T wave scores for all sensing vectors over all time as a simple continuous metric of ischemia level. One could modify the integral with weights so that high levels of ischemia scores are weighted disproportionately to the overall scale.

The continuous metric (CM) may be expressed as below:

$$CM = \int_{T_O}^{present} W_1 |STS_N| + W_2 TS_N \, dt$$

where $STS_N$ is the total normalized ST segment score, $TS_N$ is the total normalized T wave score, $W_1$ and $W_2$ are weight factors.

The foregoing may be utilized to advantage in formulating a diagnosis. For example, a bin classification by heart rate, posture and activity may be provided. Added to this may be recent history. The posture detector may be of the type previously described.

Heart rate may be classified as low or high, while the posture may be classified as horizontal or vertical. Activity may be classified as high or low. This gives rise to the chart in the following Table 1.

TABLE 1

| Case | HR | Posture | Activity | Possible Indications With High ST Segment or T Wave Scores |
|---|---|---|---|---|
| 1 | Low | Horizontal | Low | MI, Spasm |
| 2 | Low | Horizontal | High | Pacer Malfunction |
| 3 | Low | Vertical | Low | MI, Spasm |
| 4 | Low | Vertical | High | Pacer Malfunction |
| 5 | High | Horizontal | Low | MI and Panic |
| 6 | High | Horizontal | High | Sexual or Weight Lifting |
| 7 | High | Vertical | Low | MI and Panic |
| 8 | High | Vertical | High | Exercise Ischemia |

From Table 1 it may be seen that an MI or a spasm is indicated with a high ST or T wave score and low heart rate, horizontal posture, and low activity. With a high ST or T wave score and low heart rate, horizontal posture, and high activity, a device malfunction is indicated. Hence, the current patient condition may be classified by the ST and T wave scores and heart rate, posture and activity level.

Figure 5:
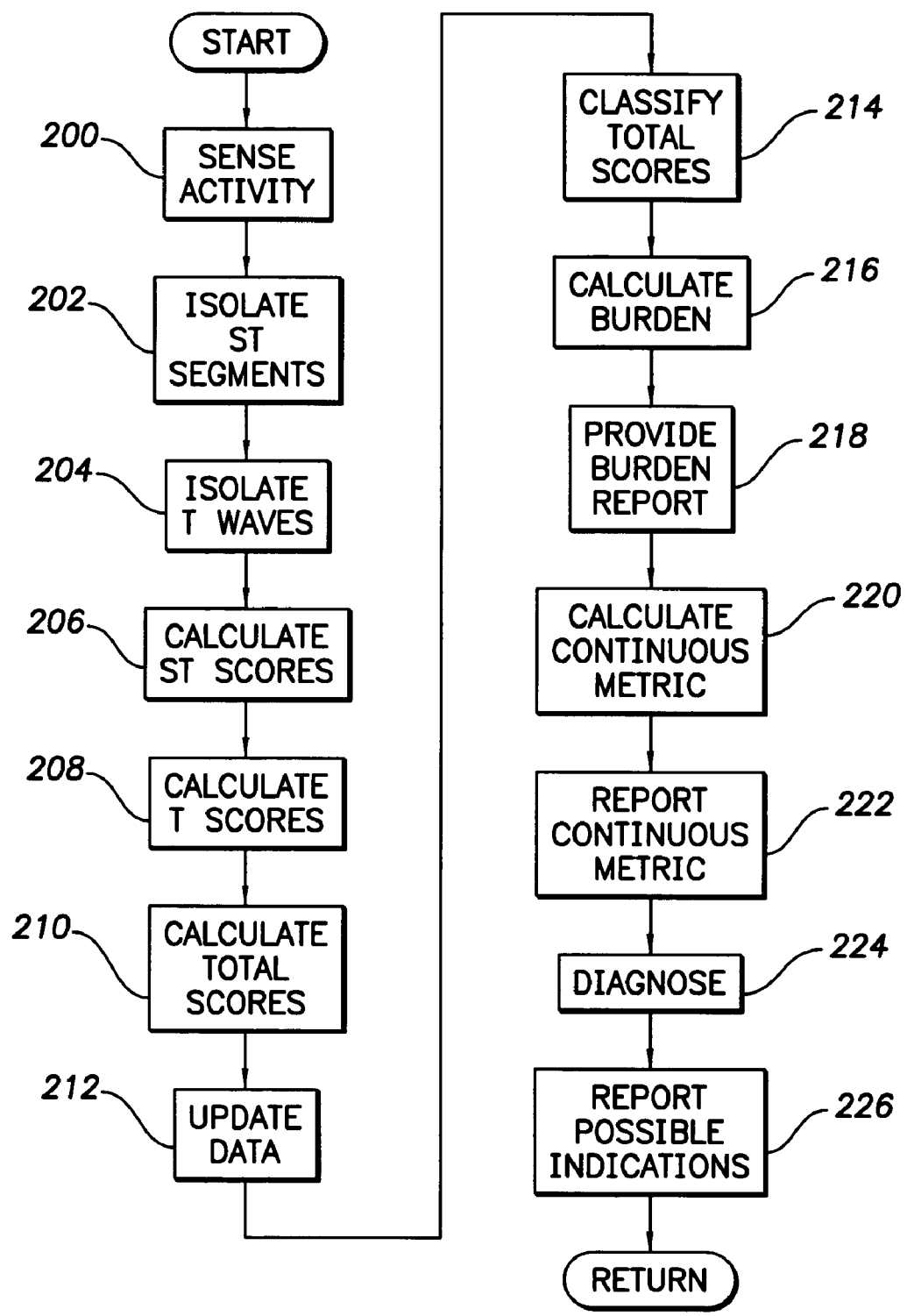
FIG. 5 shows a flowchart of a method of monitoring and detecting ischemia according to an illustrative embodiment.

FIG. 5 is a flowchart illustrating an overview of the operation and novel features implemented in one embodiment of the device 10 in accordance with the present invention. In this flowchart, the various algorithmic steps are summarized in individual "blocks". Such blocks describe specific actions or decisions that must be made or carried out as the algorithm proceeds. Where a microcontroller (or equivalent) is employed, the flowchart presented herein provides the basis for a "control program" that may be used by such a microcontroller (or equivalent) to effectuate the desired control of the stimulation device. Those skilled in the art may readily write such a control program based on the flowchart and other descriptions presented herein.

The process of FIG. 5 initiates with activity block 200 wherein cardiac activity for a cardiac cycle is sensed utilizing a plurality of sensing electrode configurations as previously described. Each electrode configuration provides an electrogram which is digitized by the data acquisition system 90 and stored in memory 94. The process then advances to activity block 202 wherein the ST segments of the electrograms are isolated. As previously mentioned, the morphology detector 61 may be utilized to advantage in isolating the ST segments. After activity block 202, the process advances to activity block 204 wherein, similarly, the T waves of the electrograms are isolated.

Once the ST segments and T waves are isolated, the process advances to activity block 206 wherein the ST segment score for each electrogram is calculated. Similarly, in activity block 208, the T wave score for each electrogram is calculated. Once the ST segment and T wave scores are calculated, the process advances to activity block 210 wherein the total ST segment score and total T wave score are calculated. With the total ST segment score and total T wave score calculated, the process advances to activity block 212 wherein the individual ST segment scores, individual T wave segment scores, and the total ST segment and T wave scores are stored in memory for later use. Next, in activity block 214, the total ST segment score and total T wave score are classified using, for example, one of the metrics previously described. Next, in activity block 216, the ischemia burden is calculated. As previously described, the ischemia burden may be the percentage of metric results indicating a myocardial infarctions, exercise induced ischemia, or no detected ischemia. Following activity block 216, the burden report is next provided in activity block 218. The burden report may be formatted by the report formatter 67 and conveyed to either memory 94 for later transmission by the telemetry circuit 100 or directly to the telemetry circuit 100 for transmission. The burden report may also be utilized for initiating therapy. Such therapy initiation may occur if one of the percentages indicating a myocardial infarction or exercise induced ischemia exceeds a predetermined value.

The process next proceeds to activity block 220 wherein the continuous metric is calculated. The continuous metric may be calculated as previously described. Next, in activity block 202, the continuous metric is reported by the report formatter 67. Once the continuous metric is reported, the process advances to activity block 224 wherein the current patient condition is diagnosed. The diagnosis may be accomplished as previously described, for example, with reference to Table 1. Lastly, in activity block 226, the possible indications resulting from the diagnosis of activity block 224 is reported by the report formatter 67. Again, the possible indications may be stored in memory 94 for later transmission by telemetry circuit 100, or may be conveyed directly to the telemetry circuit 100 for immediate transmission.

In accordance with the present invention, whenever a report is made which indicates that there exists a high or extreme ischemic condition of the patient, an alert may be provided to the patient. Such an alert may be used to inform the patient that the patient' physician should be consulted. The alert may be in the form of a vibrating transducer, for example, discernable by the patient. Further, along with or alternatively to the alert, the device may be activated to provide suitable therapy to maintain appropriate cardiac output during the ischemic event. Such therapies are varied and are well known in the art.

While the ischemia detection system has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein. For example, while the ischemia detection system has been described as a fully implanted system, it will be apparent to those skilled in the art that the detection scheme described herein may also be incorporated into external devices, such as temporary pacemakers and other external devices that are connected to implanted leads or to leads placed externally on the patient's body.

What is claimed is:

1. In a cardiac monitoring device, a method of detecting ischemia of a heart comprising:
    sensing cardiac activity of the heart to provide an electrogram of the cardiac activity;
    integrating a selected feature of the electrogram to provide an integral;
    normalizing the integral by a normalizing factor to provide an electrogram feature score; and
    providing an ischemia indication when the electrogram feature score satisfies a given criteria, wherein sensing comprises providing a plurality of electrograms, and wherein the method further comprises providing a like plurality of electrogram feature scores and combining the electrogram feature scores to provide a combined electrogram feature score, and wherein providing comprises analyzing the combined electrogram feature score.

2. An ischemia detecting device comprising:
    at least two electrodes that sense cardiac activity of a heart;
    a sensing circuit coupled to the at least two electrodes that provides an electrogram of the sensed cardiac activity;
    a processor comprising an integrator that provides an integral of a selected feature of the electrogram and a normalizer that normalizes the integral by a normalizing factor to provide an electrogram feature score; and
    an analyzer that provides an ischemia indication when the electrogram feature score satisfies a given criteria,
    wherein the at least two electrodes provide a plurality of cardiac activity sensing electrode configurations resulting in a plurality of electrograms and electrogram feature scores, wherein the processor further comprises a combiner that provides a combined electrogram feature score, and wherein the analyzer analyzes the combined electrogram feature score.

3. The device of claim 2 wherein the selected electrogram feature is at least one of an ST segment and a T wave.

4. The device of claim 2 wherein the normalizing factor is one of an R wave amplitude and an R wave amplitude difference.

5. The device of claim 2 wherein the normalizer is a divider and wherein the divider further divides the integral by a time duration of the selected feature.

6. The device of claim 2 wherein the sensing circuit and processor are enclosed within a conductive case and wherein the at least two electrodes include the case.

7. The device of claim 5 wherein the at least two electrodes further include one of a ring electrode and a tip electrode.

8. The device of claim 2 wherein the at least two electrodes are a ring electrode and a tip electrode.

9. The device of claim 2 wherein the combiner is a summer that adds the electrogram feature scores to provide the combined electrogram feature score.

10. The device of claim 2 wherein the combiner selects a maximum one of the electrogram feature scores as the combined electrogram feature score.

11. The device of claim 2 wherein the normalizer normalizes the combined electrogram feature score by a second normalizing factor.

12. The device of claim 11 wherein the second normalizing factor is heart rate.

13. The device of claim 2 wherein the analyzer applies a threshold metric to the combined electrogram feature score.

14. The device of claim 13 wherein a combined electrogram feature score is provided by the device for each one of a plurality of cardiac cycles, and wherein the device further comprises a reporter that reports a percentage of the combined feature scores which exceed the threshold metric.

15. The device of claim 2 wherein the analyzer provides a continuous metric of the combined electrogram feature scores.

16. The device of claim 2 further comprising a classifier that classifies the combined electrogram feature scores by one of heart rate, posture and activity level.

17. An ischemia detecting device comprising:
    sensing means for sensing cardiac activity from a plurality of electrodes to provide a plurality of electrograms of the sensed cardiac activity;
    integrating means for integrating a selected feature of the plurality of electrograms to provide a plurality of integrals;
    normalizing means for normalizing the plurality of integrals by a normalizing factor to provide a plurality of electrogram feature scores;
    a combiner that provides a combined electrogram feature score; and
    detecting means for detecting ischemia when the combined electrogram feature score satisfies a given criteria.

* * * * *